United States Patent [19]
Giles et al.

[11] Patent Number: 6,069,257
[45] Date of Patent: May 30, 2000

[54] PROCESS FOR THE PRODUCTION OF TETRAZOLYLBENZOPYRANS

[75] Inventors: Robert Gordon Giles; Norman John Lewis; Paul Oxley, all of Kent; John Kirby Quick, Crowborough, all of United Kingdom

[73] Assignee: SmithKline Beecham p.l.c., Bretford, United Kingdom

[21] Appl. No.: 09/341,200

[22] PCT Filed: Dec. 30, 1997

[86] PCT No.: PCT/EP97/07341

§ 371 Date: Jul. 6, 1999

§ 102(e) Date: Jul. 6, 1999

[87] PCT Pub. No.: WO98/30559

PCT Pub. Date: Jul. 16, 1998

[30] Foreign Application Priority Data

Jan. 9, 1997 [GB] United Kingdom .................. 9700331

[51] Int. Cl.[7] .................................................. C07D 405/04
[52] U.S. Cl. ........................................... 548/251; 548/253
[58] Field of Search ..................... 548/251, 253

[56] References Cited

FOREIGN PATENT DOCUMENTS

WO 94/12492  6/1994  WIPO .

OTHER PUBLICATIONS

H. Dziklinska et al., Bull. Soc. Chim. Belg., vol. 98, No. 4, 1989, pp. 227–284, XP002065412, fig. 4, Compound G.

*Primary Examiner*—Laura L. Stockton
*Attorney, Agent, or Firm*—James M. Kanagy; Charles M. Kinzig

[57] ABSTRACT

A process for preparing certain substituted benzopyran compounds of formula (I)

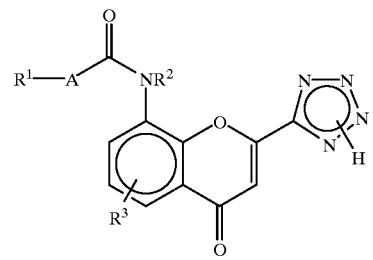

is disclosed.

13 Claims, No Drawings

PROCESS FOR THE PRODUCTION OF TETRAZOLYLBENZOPYRANS

This application is a 371 of PCT/EP97/07341 filed Dec. 30, 1997.

The present invention relates to a process for preparing substituted benzopyran compounds known in the art as therapeutic agents and the novel preparation of intermediates useful in the process. The invention also relates to novel compounds useful as therapeutic agents.

Substituted benzopyran compounds are known in the art. For example EP 0 173 516-A discloses a class of substituted benzopyran compounds which are described as compounds having activity as leukotriene antagonists and 5-a-reductase inhibitors and useful in therapy in the treatment of diseases caused or exacerbated by leukotrienes or 5-a-reductase activity.

In particular the compound 4-oxo-8-[4-(4'-phenylbutoxy)benzoylamino]-2-(tetrazol-5-yl)-4H-1-benzopyran which has the INN pranlukast is being developed as an anti-asthma agent. Various procedures for preparing such compounds are known in the art, however some procedures suffer from certain disadvantages when considered for large scale commercial application. In particular the procedures known in the art are multi-step syntheses and there is therefore need for an improved route which gives the desired compounds in good yield with relatively few process steps.

In a first aspect is therefore provided a process for the preparation of a compound of structure (I):

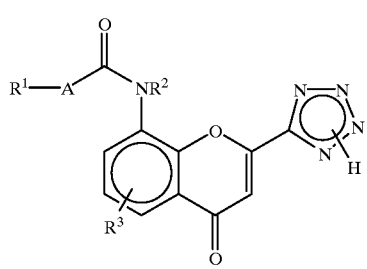

(I)

in which, $R^1$ is $C_{1-20}$alkyl, $C_{2-20}$alkenyl, $C_{2-20}$alkynyl, or a group of structure:

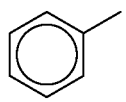

(i)

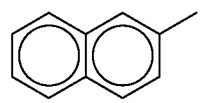

(ii)

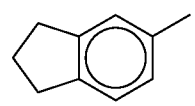

(iii)

each of which may be substituted by one or two substituents selected independently from $C_{1-20}$alkyl, $C_{2-20}$alkenyl or $C_{2-20}$alkynyl, up to 5 carbon atom(s) of which may optionally be replaced by oxygen atom(s), sulphur atom(s), halogen atom(s), nitrogen atom(s), benzene ring(s), thiophene ring(s), naphthalene ring(s), carbocyclic ring(s) of from 4 to 7 carbon atom(s), carbonyl group(s), carbonyloxy group(s), hydroxy group(s), carboxy group(s), azido group(s) and/or nitro group(s):

$R^2$ is hydrogen or $C_{1-6}$alkyl;

$R^3$ is hydrogen, halogen, hydroxy, nitro, a group of general formula —$COOR^6$ (wherein $R^6$ represents hydrogen or $C_{1-6}$alkyl), $C_{1-6}$alkyl, $C_{1-6}$alkoxy or $C_{1-6}$alkylthio;

A is a single bond or a vinylene, propenyl-1-ene, butenyl-1-ene, butadienyl-1-ene or ethynylene group optionally being substituted by one, two or three $C_{1-10}$alkyl and/or phenyl group(s); provided that the group formed by $R^1$ and A provides a double or triple bond adjacent to the carbonyl group of the compound of formula (I);

which comprises reduction of a compound of formula (II):

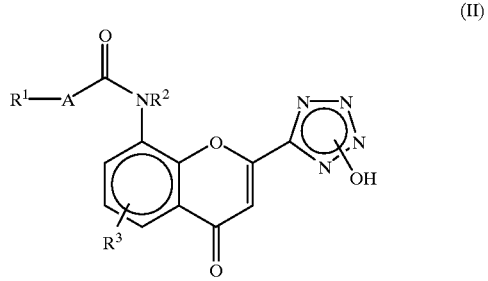

(II)

in which $R^1$, $R^2$, $R^3$ and A are as defined in formula (I) and optionally thereafter forming a pharmaceutically acceptable salt, hydrate or N-oxide.

The reduction of compounds of formula (II) is suitably carried out using a reducing agent such as tributyltin hydride+AIBN (Azodiisobutyl nitrile, 2,2'-azo-bis(2-methylpropionitrile)), DMSO+sulfuric acid, titanium trichloride+$CO_2$+HCl, powdered Fe in acetic acid, palladium+acetic acid and acetic anhydride, triphenyl phosphine, triethyl phosphite, 3-sulfolene, di-n-propyl sulfoxylate and titanium (0). Preferably the reducing agent is titanium (0). Preferably the titanium (0) is generated in situ, for example from titanium tetrachloride and lithium aluminium hydride. The reduction is suitably carried out in an inert solvent at ambient or elevated temperature. Preferably the reduction is carried out in THF at elevated temperature, for example at reflux temperature.

In particular, the reactions claimed benefits herein are useful in the preparation of compounds (I) in which $R^1$ and A form a group of formula (ii):

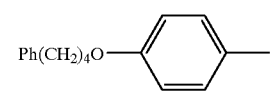

(ii)

Preferably $R^2$ and $R^3$ are both hydrogen.

Most preferably the process of the invention can be used to prepare the compound pranlukast, that is to say the compound 4-oxo-8-[4-(4'-phenylbutoxy)benzoylamino]-2-(tetrazol-5-yl)-4H-1-benzopyran or salt, hydrate or N-oxide thereof.

Compounds of formula (II) can be prepared by reaction of a compound of formula (III):

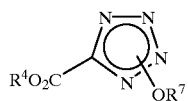

(III)

in which $R^4$ is $C_{1-6}$alkyl and $R^7$ is hydrogen, $C_{1-6}$alkyl or an alkali metal ion with a compound of formula (IV):

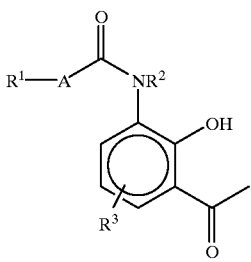

(IV)

in which $R^1$, $R^2$, $R^3$ and A are as defined in formula (I) using chemistry known in the art, for example the procedures disclosed in WO94/12492. Suitably $R^7$ is hydrogen, $C_{1-6}$alkyl or an alkali metal ion such as sodium or potassium. Preferably $R^7$ is hydrogen. Preferably this reaction is used to prepare compounds of formula (II) which is 4-oxo-8-[4-(4'-phenylbutoxy)benzoylamino]-2-(2-hydroxytetrazol-5-yl)-4H-1-benzopyran.

The N-1 hydroxytetrazole compound of formula (III) can be prepared according to literature procedures as exemplified herein. The regiospecific preparation of the N-2 hydroxytetrazole compound of formula (III) can be carried out by oxidation of a compound of formula (V):

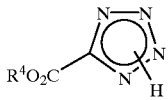

in which $R^4$ is as defined in formula (III). A compound of formula (V) is suitably treated with oxone (potassium peroxymonosulphate, $2KHSO_5.KHSO_4.K_2SO_4$) at alkali pH. Preferably the reaction is carried out at pH 7.5–8.0 in aqueous acetone. Preferably $R^4$ is an ethyl group.

In particular the process of the invention can be used to prepare the compounds of formula (II) 4-oxo-8-[4-(4-phenylbutoxy)benzoylamino]-2-(1-hydroxytetrazol-5-yl)-4H-1-benzopyran or 4-oxo-8-[4-(4-phenylbutoxy)benzoylamino]-2-(2-hydroxytetrazol-5-yl)-4H-1-benzopyran which are the preferred intermediates used to prepare the compound 4-oxo-8-[4-(4-phenylbutoxy)-benzoylamino]-2-(tetrazol-5-yl)-4H-1-benzopyran or salt, hydrate or N-oxide thereof.

In a further aspect the invention therefore provides 4-oxo-8-[4-(4-phenylbutoxy)-benzoylamino]-2-(tetrazol-5-yl)-4H-1-benzopyran or salt, hydrate or N-oxide thereof prepared using the processes disclosed herein and in particular whenever prepared from 4-oxo-8-[4-(4-phenylbutoxy) benzoylamino]-2-(1-hydroxytetrazol-5-yl)-4H-1-benzopyran or 4-oxo-8-[4-(4-phenylbutoxy)benzoylamino]-2-(2-hydroxytetrazol-5-yl)-4H-1-benzopyran.

The invention therefore provides the use of a process as herein defined for the preparation of 4-oxo-8-[4-(4-phenylbutoxy)benzoylamino]-2-(tetrazol-5-yl)-4H-1-benzopyran or a salt, hydrate or N-oxide thereof.

Compound of formula (II) are believed to be novel and form a further aspect of the invention. Compounds of formula (II) have been found to posess biological activity and the invention therefore provides a compound of formula (II) or a pharmaceutically acceptable salt or hydrate thereof for use as a therapeutic agent.

The present invention also provides a compound of general formula (II) or a physiologically acceptable salt or hydrate thereof for use in the prophylaxis or treatment of disorders in which antagonism of leukotriene activity is beneficial, in particular the treatment of asthma.

In another aspect the invention provides the use of a compound of general formula (II) or a pharmaceutically acceptable salt or hydrate thereof for the manufacture of a medicament for the treatment of the above disorders.

In a further aspect the invention provides a method of treating the aforementioned disorders which comprises administering an effective amount to a patient in need of such treatment of a compound of general formula (II) or a pharmaceutically acceptable salt or hydrate thereof.

In particular the invention provides a compound of formula (II) or a physiologically acceptable salt of hydrate thereof for use in the treatment or prophylaxis of asthma.

The present invention also provides a pharmaceutical composition, which comprises a compound of formula (II) or a pharmaceutically acceptable salt or hydrate thereof, and a pharmaceutically acceptable carrier.

A pharmaceutically composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit does form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The following examples serve to illustrate the invention.

EXAMPLE 1

Preparation of 4-Oxo-8-[4-(4-phenylbutoxy) benzoylamino]-2-(1-hydroxytetrazol-5-yl)-4H-1-benzopyran Ethyl 1-hydroxytetrazole-5-carboxylate [prepared using the literature procedure, O. A. Luk'yanoz and N. I. Shlykova, Izv. An. CCCP Cep. Xim., (1984), 181, *Chem. Abstr.* 100, 191795d, (1984); *Izv. An. CCCP Cep. Xim.*), 2540, (1987, *Chem. Abstr.* 109, 92884m, (1988).] (1.18 g, 6.3 mmole) in DMF (2 ml) was added dropwise over about 15 minutes to a mixture of 3-[4-(4'-phenylbutoxy) benzoylamino]-2-hydroxyacetophenone (1.96 g) and potassium t-butoxide (3.82 g, 34 mmole) in DMF (8 ml) at 0–5° C. The mixture was stirred at this temperature range for 1 hour. Methanol (25 ml) was added to the mixture, followed by concentrated hydrochloric acid (5 ml) and the resulting yellow suspension was heated at reflux for one and a half hours. Water (25 ml) was added and the mixture was cooled to 30° C. The product was filtered off, washed with 1:1 water-methanol and dried to give the title compound as a white solid (2.42 g, 98% yield), m.pt. 238–40° C. $^1$H NMR (400 MHz, CDCl$_3$:d$_6$-DMSO 1:1) δ9.44 (1H, s, NH), 8.56 (1H, dd, Ar—H), 7.95 (2H, d, Ar—H), 7.78, (1H, dd, Ar—H), 7.44 (1H, t, Ar—H), 7.30–7.14 (5H, m, Ar—H), 7.18 (1H, s, C(3)H), 6.93 (2H, d, Ar—H), 4.02 (2H, br. t CH$_2$—O), 1.75–1.85 (4H, m, CH$_2$CH$_2$), 2.69 (2H, br.t, ArCH$_2$)ppm; $^{13}$C NMR (100 MHz, CDCl$_3$:d$_6$DMSO 1:1) δc 176.0 (C=O, q), 164.1 (amide C=O, q), 161.6 (Ar—O, q), 149.9 (q), 146.2 (q), 141.7 (q), 138.7 (tet C-5, q), 129.0, 128.2 (q), 128.0, 127.9, 126.4, 125.2 (q), 125.0, 123.6 (q), 119.0, 113.9, 109.6, 67.4, 34.8, 28.1, 27.2 ppm; MS: positive ion electrospray m/z 498 [M+H]$^+$.

Preparation of Ethyl 2-hydroxytetrazole-5-carboxylate

To a solution of the sodium salt of ethyl tetrazole-5-carboxylate (6.56 g, 40 mmoles) in water (100 mls) was added acetone (3 ml, 40 mmole) and solid sodium bicarbonate (8.4 g, 50 mmoles). Oxone (30.74 g, 50 mmoles) was added portionwise over 5 minutes and the reaction mixture was stirred at 35° C. for 44 hours. The pH was readjusted to 5.82 with solid sodium bicarbonate and a further charge of oxone (3.1 g, 5 mmoles) was made over two minutes followed by acetone (1 ml) and the reaction mixture was stirred at 35° for a further 16 hours. The pH of the reaction mixture was adjusted to 6.5 using solid sodium bicarbonate and cooled to 10° C. Sodium metabisulphite was added, ensuring that the pH was maintained at 5.5–6.5 by the occasional addition of sodium bicarbonate, until a negative result was obtained using the merckoquant peroxide paper test.

When all the peroxide had been destroyed, the pH of the aqueous phase was adjusted to 1.0 using concentrated hydrochloric acid, and the resulting suspension was washed with isopropyl acetate (40 ml×2.20 ml×4) and the organic extracts were discarded. The pH of the aqueous phase was adjusted to 0.3 using concentrated hydrochloric acid in the presence of isopropyl acetate (40 ml). The aqueous phase was then saturated with sodium chloride and the phases separated. The aqueous was re-extracted using isopropyl acetate (40 ml, 20 ml×4). The combined organic extracts were then dried over sodium sulphate and concentrated to dryness in vacuo to give an oil which crystallised on standing (4.45 g). Analysis by HPLC showed this to be the title compound of a purity>95%. The total yield was 5.71 g (88% yield), m.pt. 75–8° C.

$^1$H NMR (400 Mhz, d$_6$-acetone) δ1.36 (3H, t, 4.42, CH$_2$CH$_3$), (2H, q, CH$_2$CH$_3$) ppm; $^{13}$C NMR (100 MHz, d$_6$-acetone) δc 157.9 (q), 154.7 (q), 62.74, 14.28 ppm; HRMS: Found 159.0515, C$_4$H$_7$N$_4$O$_3$ requires 159.0512.

EXAMPLE 2

Preparation of 4-Oxo-8-[4-(4-phenylbutoxy) benzoylamino]-2-(2-hydroxytetrazol-5-yl)-4H-1-benzopyran To a suspension of 3-[4-(4'-phenylbutoxy) benzoylamino]-2-hydroxyacetophenone (10.2 g, 25 mmoles) and ethyl 2-hydroxytetrazole-5-carboxylate (4 g, 25.3 mmoles) in THF (30 moles) was added a solution of potassium t-butoxide (17.34 g at 98.3% assay, 152 mmoles) in THF (70 mls). The reaction mixture was heated to reflux for 1 hour at which point atmospheric distillation was performed and 50 ml of distillate was collected. The reaction mixture was diluted with methanol (20 ml), cooled, and the resulting suspension was added to a solution of concentrated hydrochloric acid (19 ml, 217.6 mmoles) in methanol (85 ml) with rapid stirring. The resulting suspension was heated to reflux for 90 minutes whereupon a further charge of concentrated hydrochloric acid (8.8 ml), 100 mmole) was made and the reaction was heated at reflux for a further 16 hours. The resulting white suspension was cooled to room temperature and the product was filtered and washed with methanol (50 ml×2). The crude product was stirred in water (100 ml), filtered, washed with water (50 ml×3) and dried at 50° C. overnight to give the title compound (9.92 g, 79% yield), m.pt. 192° C. (decomp).

$^1$H NMR (400 MHz, CDCl$_3$:d$_6$-DMSO 1:1) δ9.89 (1H, s, NH), 8.22 (1H, dd, Ar—H), 8.04 (2H, d, Ar—H), 7.91 (1H, dd, Ar—H), 7.49 (1H, t, Ar—H), 7.27–7.16 (5H, m, Ar—H), 7.03 (2H, d, Ar—H), 7.01 (1H, s, C(3)H)), 4.08 (2H, br.t, CH$_2$O), 2.69 (2H, br. t, ArCH$_2$), 1.85–1.75 (4H, m, CH$_2$CH$_2$) ppm; $^{13}$C NMR (100 MHz, CDCl$_3$:d$_6$-DMSO 1:1) δ176.1 (C=O, q), 164.6 (amide C=O, q), 161.5 (q), 153.7 (q), 152.1 (net C(5), q), 148.1 (q), 141.5 (q), 129.3, 128.5, 127.9, 127.8 (q), 127.8, 125.6 (q), 125.3, 124.9, 124.0 (q), 120.4, 113.8, 108.8, 67.4, 34.7, 28.0, 27.1 ppm; HRMS: Found 498.1765, C$_{27}$H$_{24}$N$_5$O$_5$ requires 498.1770 [M+H]$^+$.

Preparation of Pranlukast from either 4-oxo-8-[4-(4-phenylbutoxy)benzoylamino]-2-(2-hydroxytetrazol-5-yl)-4H-1-benzopyran or 4-oxo-8-[4-(4-phenylbutoxy)benzoylamino]-2-(1-hydroxytetrazol-5-yl)-4H-1-benzopyran.

To a suspension of titanium tetrachloride (0.49 ml, 1.8 mole equivalents) in tetrahydrofuran (2.5 ml) was added lithium aluminium hydride (123 mg, 1.3 mole equivalents) to produce a black suspension of titanium (0) which was stirred for 15 minutes. 4-Oxo-8-[4-(4-phenylbutoxy)benzoylamino]-2-(2-hydroxytetrazol-5-yl)-4H-1-benzopyran (1.24, 1 mole equivalent) was added, together with additional tetrahydrofuran (5 ml). The mixture was stirred for 60 minutes at room temperature and then heated at reflux for 90 minutes to give pranlukast in 71% solution yield.

The same yield was obtained using 4-oxo-8-[4-(4-phenylbutoxy)benzoylamino]-2-(1-hydroxytetrazol-5-yl)-4H-1-benzopyran under the above conditions, although a reaction mixture of only 30 minutes at room temperature was required.

Pharmacological Data

Experimental Procedure for Binding Studies in Guinea-Pig Lungs with Pranlukast and Metabolites Binding studies, using [$^3$H]-LTD$_4$, were performed in guinea pig lung membranes as described previously (1). Lung membranes (5.0–2.0 ug protein), prepared from tissues obtained from male Hartley guinea pigs (Hazelton Research Animals, Denver, Pa., U.S.A.; 450–650 g body weight), were incubated in a volume of 200 ul containing PIPES (pH, 6.5; Sigma chemical Co., St. Louis, Mo., U.S.A.), 10 mM CaCl$_2$, 10 mM MgCl$_2$, 10 mM glycine (Sigma), 10 mM cysteine (Sigma) and 0.5 nM [$^3$H]-LTD$_4$ (140 Ci/mmol; New England Nuclear, Boston Mass., U.S.A.) for 30 min at 25° C. Non-specific binding was determined in the presence of 0.5 uM cold LTD$_4$. Membranes with bound ligand were captured on Whatman GF/C filters using vacuum filtration and a Brandel cell harvester, then washed with ice-cold 25 mM Tris-HCl. pH 7.4. The filters were placed in scintillation vials with 10 ml Ready Protein (Beckman, Fullerton, Calif., U.S.A.) and the radioactivity was determined by scintillation spectrometry.

Data Analysis

All data are presented as Mean±S.E.M. Concentration-response curves (0.3–10,000 nM) for each compound were tested in at least 2 assays and run in duplicate. Cell-bound radioactivity was determined for each sample and non-specific binding was established in the presence of 1 uM unlabeled LTD$_4$ and subtracted from control and drug-treated samples. The percentage inhibition of specific [$^3$H]-LTD$_4$ binding was determined for each drug concentration, and the IC$_{50}$, defined as the concentration of test compound required to inhibit 50% of specific [$^3$H]-LTD$_4$ binding, determined. Values are represented as K$_i$, which were calculated from the IC$_{50}$ as described by Cheng and Prusoff (2) using the equation:

$$K_i = \frac{IC_{50}}{[1 + [L]/K_d]}$$

where [L] is the concentration of added ligand and the K$_d$ is the ligand dissociation constant (determined from saturation studies to be 0.2 nM).

References

1. Sarau, H. M., Mong, S., Foley J. J., Wu, H. -L. and Crooke, S. T. Identification and characterization of leukotriene D$_4$ receptors and signal transduction processes in rat basophilic leukemia cells. J. Biol. Chem., 262: 4034–4041, 1987.
2. Cheng, Y. -C. and Prusoff, W. H. Relationship between the inhibition constant (K$_i$) and the concentration of inhibitors which cause 50 percent inhibition (IC$_{50}$) of an enzymatic reaction. Biochem. Pharmacol., 22, 3099–3108, 1973.

The compounds of examples 1 and 2 had Ki values in [nm] of 0.22–0.53 respectively.

What is claimed is:

1. A process for the preparation of a compound of structure (I):

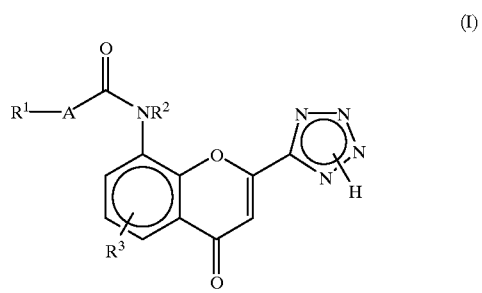

in which,

R$^1$ is C$_{1-20}$alkyl, C$_{2-20}$alkenyl, C$_{2-20}$alkynyl, or a group structure:

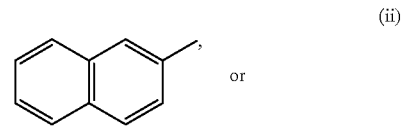

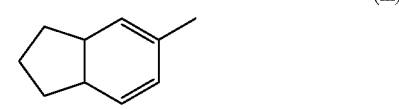

each of which may be substituted by one or two substituents selected independently from C$_{1-20}$alkyl, C$_{2-20}$alkenyl and C$_{2-20}$alkynyl, up to 5 carbon atom(s) of which may optionally be replaced by oxygen atom (s), sulphur atom(s), halogen atom(s), nitrogen atom(s), benzene ring(s), thiophene ring(s), naphthalene ring(s), carbocyclic ring(s) of from 4 to 7 carbon atom(s), carbonyl group(s), carbonyloxy group(s), hydroxy group(s), carboxy group(s), azido group(s) and/or nitro group(s):

R$^2$ is hydrogen or C$_{1-6}$alkyl;

R$^3$ is hydrogen, halogen, hydroxy, nitro, a group of general formula —COOR$^6$ (wherein R$^6$ represents hydrogen or C$_{1-6}$alkyl), C$_{1-6}$alkyl, C$_{1-6}$alkoxy or C$_{1-6}$alkylthio;

A is a single bond or a vinylene, propenyl-1-ene, butenyl-1-ene, butadienyl-1-ene or ethynylene group optionally being substituted by one, two or three $C_{1-10}$alkyl and/or phenyl group(s): provided that the group formed by $R^1$ and A provides a double or triple bond adjacent to the carbonyl group of the compound of formula (I);

which comprises reduction of a compound of formula (II):

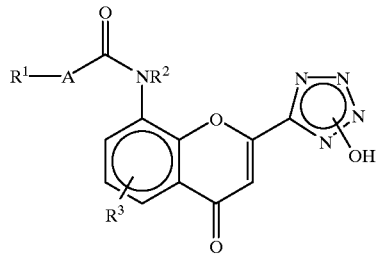

(II)

in which $R^1$, $R^2$, $R^3$ and A are as defined in formula (I) and optionally thereafter forming a pharmaceutically acceptable salt.

2. A process according to claim 1 in which $R^1$ and A form a group of formula (ii):

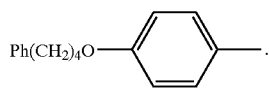

(ii)

3. A process according to claim 1 in which $R^2$ is hydrogen.

4. A process according to claim 1 in which $R^3$ is hydrogen.

5. A process according to claim 1 in which the reducing agent is tributyltin hydride+2,2'-azo-bis(2-methylpropionitrile), DMSO+sulfuric acid, titanium trichloride+$CO_2$+HCl, powdered Fe in acetic acid, palladium+acetic acid and acetic anhydride, triphenyl phosphine, triethyl phosphite, 3-sulfolene, di-n-propyl sulfoxylate and titanium (0).

6. A process according to claim 1 in which the reducing agent is titanium (0).

7. A process according to claim 6 in which reducing agent is titanium (0) generated in situ from titanium tetrachloride and lithium aluminium hydride.

8. A process according to claim 1 in which the compound prepared is 4-oxo-8-[4-(4'-phenylbutoxy)-benzoylamino]-2-(tetrazol-5-yl)-4H-1-benzopyran or salt, hydrate or N-oxide thereof.

9. A process according to claim 1 in which the compound of formula (II) is predominantly the 1-hydroxytetrazole derivative.

10. A process according to claim 1 in which the compound of formula (II) is predominantly the 2-hydroxytetrazole derivative.

11. A compound of formula (II) or a pharmaceutically acceptable salt or hydrate thereof:

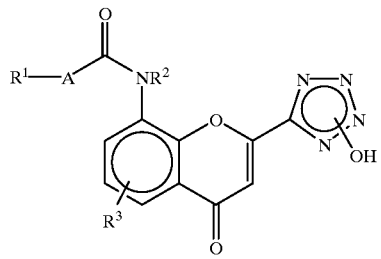

(II)

in which
$R^1$ is $C_{1-20}$alkyl, $C_{2-20}$alkenyl, $C_{2-20}$alkynyl, or a group of structure:

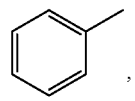

(i)

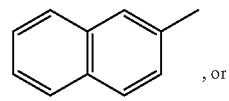

, or (ii)

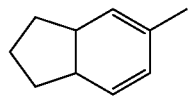

(iii)

each of which may be substituted by one or two substituents selected independently from $C_{1-20}$alkyl, $C_{2-20}$alkenyl and $C_{2-20}$alkynyl, up to 5 carbon atom(s) of which may optionally be replaced by oxygen atom (s), sulphur atom(s), halogen atom(s), nitrogen atom(s), benzene ring(s), thiophene ring(s), naphthalene ring(s), carbocyclic ring(s) of from 4 to 7 carbon atom(s), carbonyl group(s), carbonyloxy group(s), hydroxy group(s), carboxy group(s), azido group(s) and/or nitro group(s);

$R^2$ is hydrogen or $C_{1-6}$alkyl;

$R^3$ is hydrogen, halogen, hydroxy, nitro, a group of general formula —$COOR^6$ (wherein $R^6$ represents hydrogen or $C_{1-6}$alkyl), $C_{1-6}$alkyl, $C_{1-6}$alkoxy or $C_{1-6}$alkylthio;

A is a single bond or a vinylene, propenyl-1-ene, butenyl-1-ene, butadienyl-1-ene or ethynylene group optionally being substituted by one, two or three $C_{1-10}$alkyl and/or phenyl group(s): provided that the group formed by $R^1$ and A provides a double or triple bond adjacent to the carbonyl group of the compound of formula (I).

12. A compound of formula (II) which is:
4-oxo-8-[4-(4-phenylbutoxy)benzoylamino]-2-(1-hydroxytetrazol-5-yl)-4H-1-benzopyran, or
4-oxo-8-[4-(4-phenylbutoxy)benzoylamino]-2-(2-hydroxytetrazol-5-yl)-4H-1-benzopyran, or a pharmaceutically acceptable salt or hydrate thereof.

13. A pharmaceutical composition comprising a compound according to claim 11 or a pharmaceutically acceptable salt or hydrate thereof in association with a pharmaceutically acceptable carrier.

* * * * *